United States Patent [19]
Hooks et al.

[11] Patent Number: 5,529,771
[45] Date of Patent: Jun. 25, 1996

[54] LEUKOREGULIN ANTI-HERPES TREATMENT

[75] Inventors: John J. Hooks, Olney; Charles H. Evans, Potomac; Barbara Detrick, Olney, all of Md.

[73] Assignee: The United States of America as represented by the Department of Health and Human Services, Washington, D.C.

[21] Appl. No.: 348,838

[22] Filed: Nov. 29, 1994

Related U.S. Application Data

[63] Continuation of Ser. No. 521,706, May 11, 1990, Pat. No. 5,368,853.

[51] Int. Cl.$^6$ .......................... A61K 38/19; A61K 38/17
[52] U.S. Cl. .............................. 424/85.1; 514/8; 530/351
[58] Field of Search ................................ 424/85.1; 514/4, 514/8, 21; 530/351

[56] References Cited

U.S. PATENT DOCUMENTS 5,368,853  11/1994  Hooks et al. .......................... 424/85.1

OTHER PUBLICATIONS

Joklik et al, pp. 746–754 in *Zinsser Microbiology*, 15th Ed., (Appleton–Century–Crofts 1972).

Lennette et al, *Manual of Clinical Microbiology*, 4th Ed., pp. 694–700, 705–710, 711, 720, 728, 733–734, 742, 743, 747–748, 755–756, 763–764, 769, 774, 779, 785, 796–798, 805–806, 813–815, 836–837, 840–841, (Acad. Soc. Microbiol. 1985).

Lopez, "Clinical Evaluation of Anti–HIV Drugs", pp. 344–345 in *AIDS: Anti–HIV Agents, Therapies, and Vaccines*, NYAS (1990).

Gardner et al, "Animal Models of AIDS", *FASEB J.* 3: 2593–2606 (Dec. 1989).

Davis et al, *Microbiology*, 4th Ed., (Lippincott 1990) pp. 845–883.

*Primary Examiner*—Stephen G. Walsh
*Attorney, Agent, or Firm*—Townsend and Townsend and Crew

[57] ABSTRACT

The present invention relates to a method of treating a viral infection in an animal. The method comprises administering to said animal leukoregulin alone or in combination with an anti-viral chemotherapeutic agent. Herpes virus and herpes simplex virus infections are tested. The invention further relates to a pharmaceutical composition suitable for use in such a method.

2 Claims, 3 Drawing Sheets

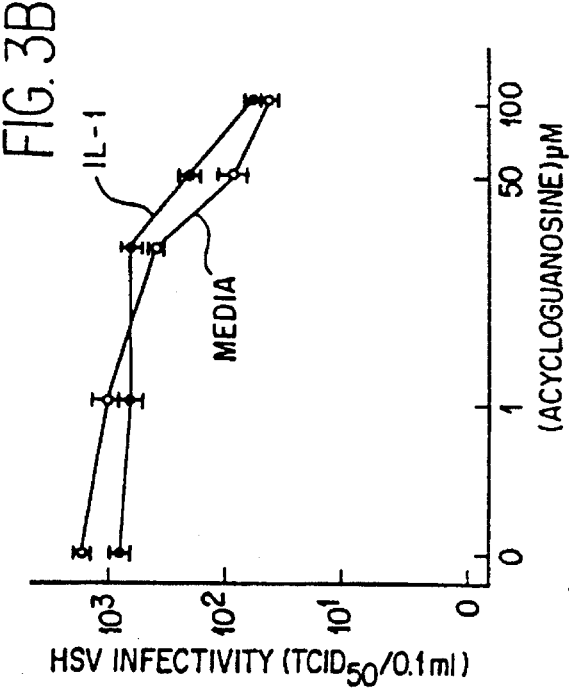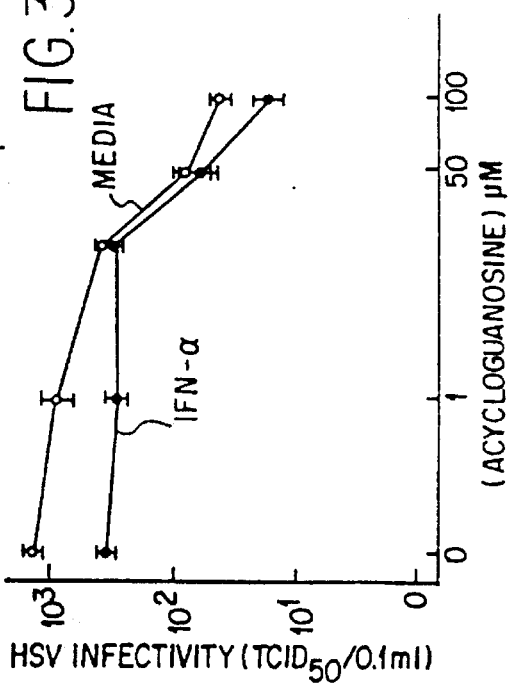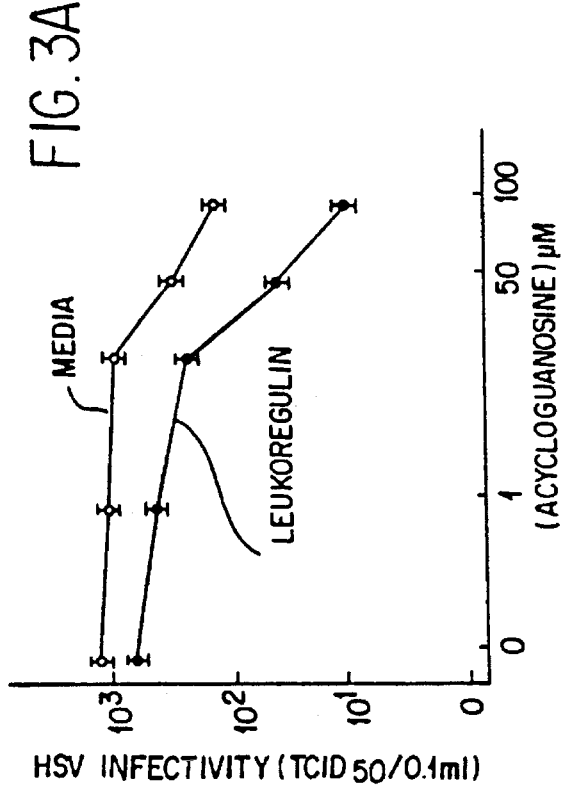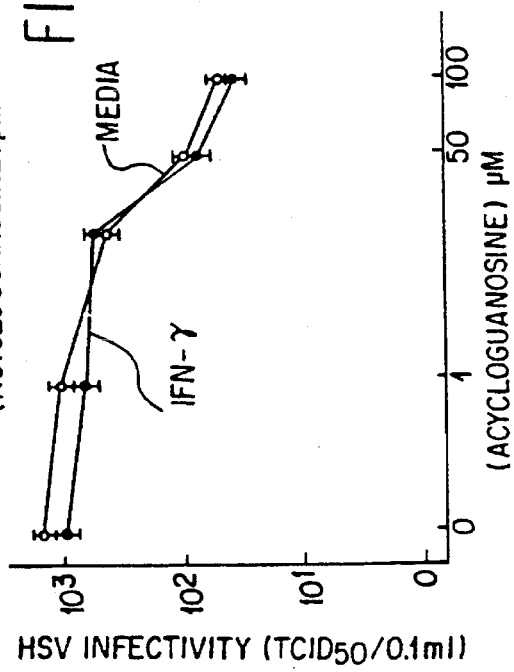

LEUKOREGULIN ANTI-HERPES TREATMENT

This application is a continuation of application Ser. No. 07/521,706, filed May 11, 1990 now U.S. Pat. No. 5,368,853.

BACKGROUND OF THE INVENTION

1. Technical Field

The present invention relates, in general to anti-viral therapy, and, in particular, to a method of inhibiting viral production which involves the use of the cytokine, leukoregulin.

2. Background Information

Herpesvirus infections are responsible for a wide spectrum of acute and recurrent diseases affecting millions of individuals throughout the world (Johnson et al, N. Engl. J. Med. 1989, 321:7–12; Corey et al, N. Engl. J. Med. 1986, 314:686–91, 749–57). The need for effective drug treatment and prevention of herpesvirus and other viral diseases has assumed growing importance. The increasing prevalence of AIDS and HIV associated infections, in addition, has stimulated a renewed interest in antiviral chemotherapy (Crumpacker, N. Engl. J. Med. 1989, 321:163–172).

During the past five years it has become clear that a single mode of therapy for virus infections may not be as effective as combination therapy. Major support for this conclusion is the development of cytokines and other "biological response modifiers" in the combined use of chemotherapy to treat various malignancies (Foon, Can. Res. 1989, 49:1621–39). With this background, studies were initiated to determine if a new cytokine, leukoregulin, which increases drug uptake in cancer cells might be useful to enhance anti-viral chemotherapy. (See U.S. Pat. No. 4,849,506.) Since acycloguanosine (ACG; 9-(2-hydroxyethoxymethyl)guanine) is active against human herpesviruses both in vitro and in vivo, ACG inhibition of acute herpesvirus production was selected as a model system to test the ability of leukoregulin to enhance anti-viral chemotherapeutic action (Elion, New Directions for Clinical Application and Research in Antiviral Chemotherapy. J. Mills & L. Corey, Eds. (Elsevier, New York, 1986) pp 118–137; Elion, Sci. 1989, 244:41–47; Crumpacker et al, Antimicrobiol. Agents & Chem. 1979, 15:642–645; and Erlich et al, N. Engl. J. Med. 1989, 320:293–6).

Leukoregulin, first described in 1984, is a lymphokine possessing unique regulatory activities for transformed cells (Ransom et al, Cancer Res. 1985, 45:851–862; Evans, Leukoregulin mechanisms of anticancer action. In Leukolysins and Cancer (Ransom, J. H., Ortaldo, J. R. eds.) The Humana Press, Inc., Clifton, N.J. 1988, pp 198–216). Today, it is apparent that this cytokine has a multifunctional nature which is reflected in the variety of its biologic activities. Leukoregulin can prevent chemical carcinogen transformation, inhibit neoplastic cell proliferation and augment target cell sensitivity to natural killer (NK) cell cytotoxicity (Evans, Leukoregulin mechanisms of anticancer action. In Leukolysins and Cancer (Ransom, J. H., Ortaldo, J. R. eds.) The Humana Press, Inc., Clifton, N.J. 1988, pp 198–216). More recently, this cytokine has been shown to increase membrane permeability of tumor cells and to increase drug uptake (Barnett et al, Cancer Res. 1986, 46:2686–92; Evans et al, J. Nat. Cancer Inst. 1988, 80:861–4). The ability of leukoregulin to enhance drug uptake occurs concomitantly with the increase in membrane permeability in tumor cells but not in normal cells.

It will be clear from a reading of the disclosure that follows that leukoregulin enhances membrane permeability of cells acutely infected with virus. This represents a hitherto unrecognized biological role for leukoregulin i.e., its ability to recognize and alter acutely virally infected cells. Treatment with leukoregulin can, therefore, be used to target entry of pharmacologically active agents into virus infected cells. The permeableness of virus infected-cells and associated enhanced drug effectiveness provides an alternative approach to the targeting of drugs for infections induced by viruses such as papillomavirus, cytomegalovirus and the human immunodeficiency virus (HIV).

The present invention thus provides a method of treating viral infection which, in one embodiment, is based on the combined use of immunotherapy (specifically, leukoregulin therapy) and anti-viral chemotherapy.

SUMMARY OF THE INVENTION

It is an object of the present invention to provide a method of inhibiting in an animal production of an infectious virus.

It is another object of the invention to provide a pharmaceutical composition suitable for use in the above method.

In one embodiment, the present invention relates to a method of treating a viral infection in an animal comprising administering to the animal:

i) an amount of leukoregulin sufficient to increase the permeability of cells of the animal infected with the virus, and ii) an amount of anti-viral chemotherapeutic agent sufficient to inhibit production of the virus in said permeabilized cells, under conditions such that the treatment is effected.

In another embodiment, the present invention relates to an anti-viral composition comprising:

i) an amount of leukoregulin sufficient to permeabilize cells of an animal infected with a virus;

ii) an amount of an anti-viral chemotherapeutic composition sufficient to inhibit production of the virus in the permeabilized cells; and iii) a pharmaceutically acceptable carrier.

Further objects and advantages of the present invention will be clear from a reading of the description that follows.

BRIEF DESCRIPTION OF THE DRAWINGS

FIG. 3 Comparative efficacy of leukoregulin, IL-1 alpha, IFN-gamma or IFN-alpha in increasing the ability of ACG to inhibit production of infectious HSV-1 by WISH cells. WISH cells were infected with HSV-1 and 3 hours later treated with ACG alone or with ACG together with 2u IL-1 alpha, 100 u IFN-gamma, or 100 u IFN-alpha for 2 hours. WISH cell culture media from triplicate samples were analyzed after 24 hours for infectious HSV-1. The values shown are the mean+2 SE. The leukoregulin results (upper left panel) are the mean of 2 separate experiments, separate from those illustrated in FIGS. 1 and 2.

DETAILED DESCRIPTION OF INVENTION

Figure 1:
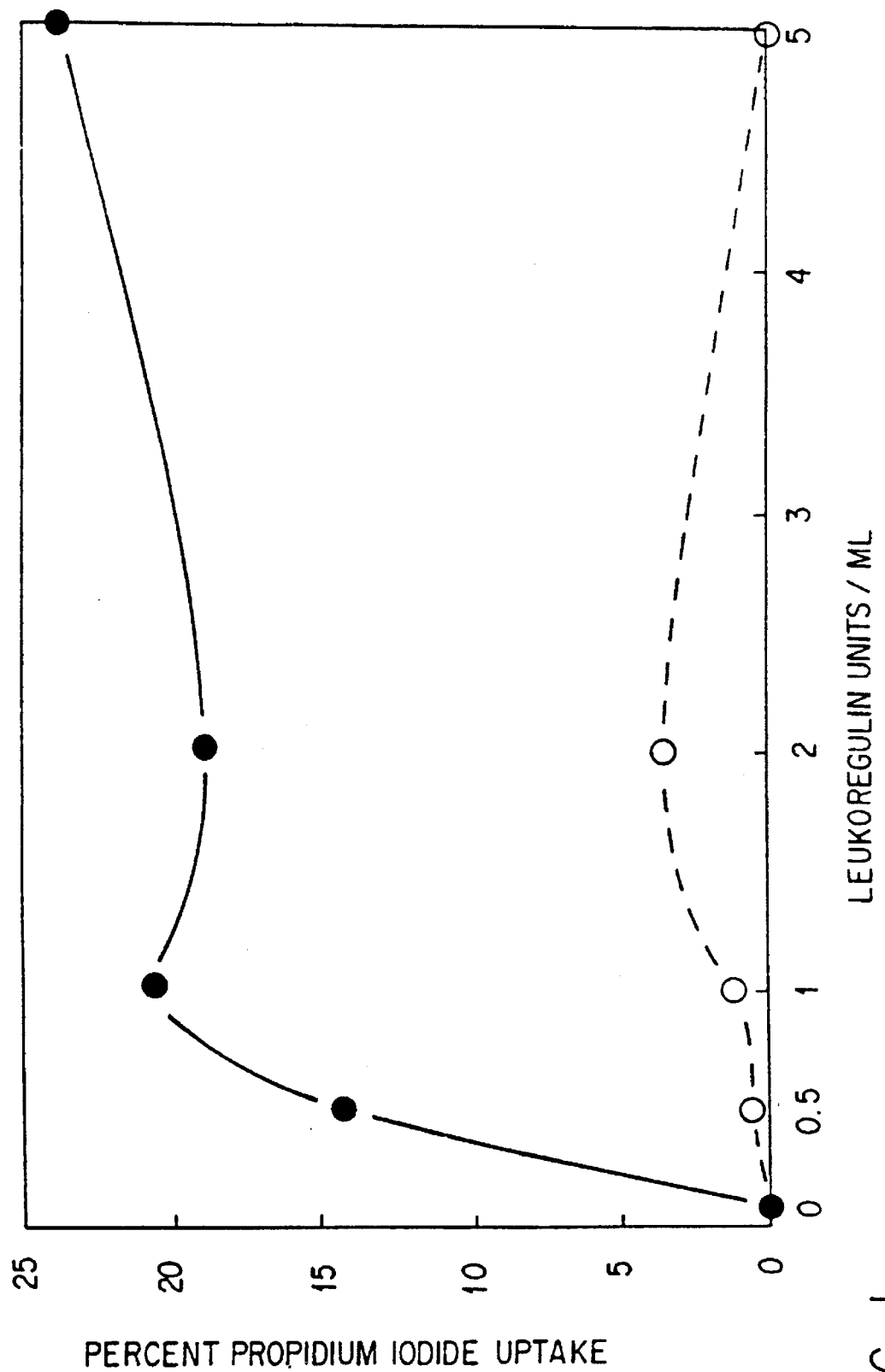
FIG. 1 Ability of leukoregulin to increase plasma membrane permeability of human amnion (WISH) cells acutely infected with HSV-1. Uptake of propidium iodide as a measure of membrane permeability was determined flow cytometrically for WISH cells 5 hours after HSV-1 virus inoculation. (o) WISH cells, (●) HSV-1 infected WISH cells.

The present invention relates, in general, to a method of inhibiting viral production. Specifically, the invention relates to the use of the cytokine, leukoregulin, alone, or in combination with an anti-viral chemotherapeutic compound, to completely inhibit the production of virus by infected cells.

The Examples that follow relate specifically to Herpes simplex viral infection. One skilled in the art will appreciate, however, that the present invention is equally applicable to treatment of infection with any enveloped virus, including hepatitis B virus, human immunodeficiency virus, cytomegalovirus, papillomavirus, etc. Further, the invention is not limited to the use of leukoregulin in combination with the chemotherapeutic agent acycloguanosine. Rather, leukoregulin can, when used in an immunotherapy/chemotherapy combination regime, enhance the ability of any anti-viral chemotherapeutic compound to inhibit the cellular release of infectious viral particles.

Leukoregulin can be administered prior to, simultaneous with, or subsequent to administration of the chemotherapeutic agent. Advantageously, the cytokine is administered prior to administration of the chemotherapeutic agent, the period between the administration of the two agents being sufficient for leukoregulin to initiate increased target cell membrane permeability. The optimum period can be determined by one skilled in the art without undue experimentation.

Leukoregulin, like the anti-viral chemotherapeutic agent, can be administered, for example, intravenously, together with a pharmaceutically acceptable carrier, to an animal (e.g., a mammal) in need of such treatment. The optimum concentration of the cytokine in the composition and total delivered dose can readily be determined by one skilled in the art. It will be appreciated that the amount of chemotherapeutic agent to be administered can be optimized by one skilled in the art for any particular treatment program.

Leukoregulin, like the anti-viral chemotherapeutic agent, can also be administered topically to an animal in need of such treatment. The composition can take the form of a lotion, gel, ointment, foam or cream. For topical administration, the total delivered dose is, advantageously, 1000 to 100,000 units (1 unit being equal to that quantity of leukoregulin that increases membrane permeability in 50% of K562 human leukemia cells (Barnett et al, Cancer Res. 1986, 46:2686–92)).

The invention relates, in addition to the above-described method of treatment, to a pharmaceutical composition comprising: i) leukoregulin in an amount sufficient to increase permeability of the plasma membrane of animal cells infected with a virus; ii) an anti-viral chemotherapeutic agent in an amount sufficient to inhibit production of the virus; and iii) a pharmaceutically acceptable carrier.

The following non-limiting Examples describe certain aspects of the invention in greater detail.

EXAMPLES

The following technical details are relevant to the Examples that follow.

Leukoregulin & Other Cytokines 50 kDa leukoregulin with a pI of 5.1 was purified from the cytokines secreted by phytohemagglutinin stimulated freshly isolated human peripheral mononuclear leukocytes using sequential DEAE-anion exchange, Rotofor horizontal column isoelectric focusing and spherical silica gel high performance liquid chromatography as described by Evans et al (Evans et al, Anal. Biochem. 1989, 117:358–363).

Recombinant human IFN-alpha (specific activity $1 \times 10^9$ units/mg protein) and recombinant INF-gamma (specific activity $1 \times 10^7$ units/mg protein) were obtained from Amgen Biologics, Thousand Oaks, Calif. Recombinant human alpha IL-1 ($10^8$ units/mg) was obtained from Genzyme Corp., Boston, Ma. Antiviral activities of the IFN preparations were determined by the reduction in vesicular stomatitis virus plaque formation on WISH cells grown in microtiter plates (Hooks et al, N. Engl. J. Med. 1979, 301:5–8). The antiviral activity, expressed in IFN units, was calculated as the reciprocal of the highest dilution of the sample that reduced the number of viral plaques by 50%.

Virus Preparation

Herpes simplex virus type-1 (HSV-1) was isolated from intraoral lesions from a 13 year old female patient with primary intraoral herpes infection at the National Institutes of Health. The virus was subcultured 3 times in primary rabbit kidney cells and 4 times in human amnion (WISH) cells (American Type Culture Collection, Rockville, Md. #CCL25). HSV infectivity titrations, tissue culture infectious doses$_{50}$ (TCID$_{50}$/0.1 ml), were performed in WISH cells maintained in 96 well microtiter plates. Each dilution was evaluated in quadruplicate. HSV infectivity titrations in terms of plaque forming units were performed in WISH cells maintained in 75 mm tissue culture dishes (Crumpacker et al, Antimicrobiol. Agents & Chem. 1979, 15:642–645).

Drugs

Acycloguanosine (ACG; 9-(2-hydroxyethoxymethyl)guanine) was obtained from Sigma Chemical Co., St. Louis, Mo.

Example I

Measurement of WISH Cell Membrane Permeability

Previous studies show that leukoregulin enhances membrane permeability in tumor cells without altering membrane permeability in "normal", non-transformed cells Human amnion WISH cells were infected with HSV-1 virus to determine if acute virus infection would render cells susceptible to the membrane permeability actions of leukoregulin.

Membrane permeability was measured flow cytometrically by the ability of WISH cells to exclude propidium iodide as previously described for K562 human leukemia cells (Barnett et al, Cancer Res. 1986, 46:2686–92). WISH cells at a concentration of $2 \times 10^6$ cells were placed in 12×75 mm Falcon polystyrene tubes and were infected with HSV-1 at a concentration of $5 \times 10^4$ TCID$_{50}$. Following a 90 minute adsorption period, cells were washed three times and then incubated for an additional 90 minutes in media. The cells were again washed twice in RPMI 1640 medium and treated at 37° C. with leukoregulin at 0.5, 1, 2 and 5 units/ml. After 2 hours incubation an equal volume of medium containing 40 µg propidium iodide/ml was added and the fluorescence of the cells was measured 5 minutes later using a FACS Analyzer (Becton Dickinson Immunocytometry Systems, Mountain View, Calif.). This assay of membrane permeability as indicated by the uptake of propidium iodide has a standard error of <+5% (Barnett et al, Cancer Res. 1986, 46:2686–92; Evans et al, J. Nat. Cancer Inst. 1988, 80:861–4).

As indicated above, following a 3 hour incubation period, the cells were washed and then treated with leukoregulin (0.5 to 5 units) for two hours. During this 5 hour post virus infection period of time, the virus is capable of inducing the expression of viral antigens on the surface of the infected cell without causing cell lysis or release of new infectious progeny virus (Lodmel et al, J. Exp. Med. 1973, 137:706–20; Lodmel et al, J. Exp. Med. 1974, 140:764–78). The membrane permeability of these virus infected cells and control non-infected cells was assessed by measurement of the uptake of the permeability dependent dye propidium iodide (Barnett et al, Cancer Res. 1986, 46:2686–92). The uptake of this molecule was followed spectrofluorometrically using a mercury arc lamp flow cytometer.

As is seen in FIG. 1, in the absence of leukoregulin, there is minimal uptake of propidum iodide in non-infected WISH cells or in HSV-1 infected WISH cells. The presence of leukoregulin for 2 hours dramatically increases membrane permeability in the virus infected cells. In contrast, leukoregulin does not increase the permeability of WISH cells not infected with HSV-1. These data indicate that HSV-1 virus infection rapidly alters the cell surface sufficiently for the lymphokine, leukoregulin, to enhance membrane permeability.

EXAMPLE II

Measurement of Cytokine Effects on Antiviral Chemotherapy

Since leukoregulin selectively increases membrane permeability in HSV-1 infected cells, it was important to determine if leukoregulin could directly alter HSV-1 infectivity or alternatively enhance the anti-HSV-1 replication actions of acyclovir. A concentration of 5 units of leukoregulin/ml was selected based on the results in FIG. 1 to insure a maximal increase in membrane permeability.

WISH cells were propagated in 96 well microtiter plates. HSV-1 at a concentration of $5\times10^4$ $TCID_{50}/0.1$ ml was added to each microtiter well. Following a 90 minute adsorption period, the supernatant medium was removed and the cells were washed three times. For each experiment, 0.1 ml of media, leukoregulin, ACG or leukoregulin—ACG mixtures was added to each of 5 wells of HSV-1 infected WISH cells unless otherwise specified. ACG and/or leukoregulin were added at various times. HSV infectivity titrations were performed on each of the culture medium from each well after a 24 hour period of incubation. Each dilution of WISH cell culture medium was evaluated in quadruplicate. The HSV-1 infectivity is recorded as the mean titer ($TCID_{50}/0.1$ ml) of each treatment.

Figure 2:
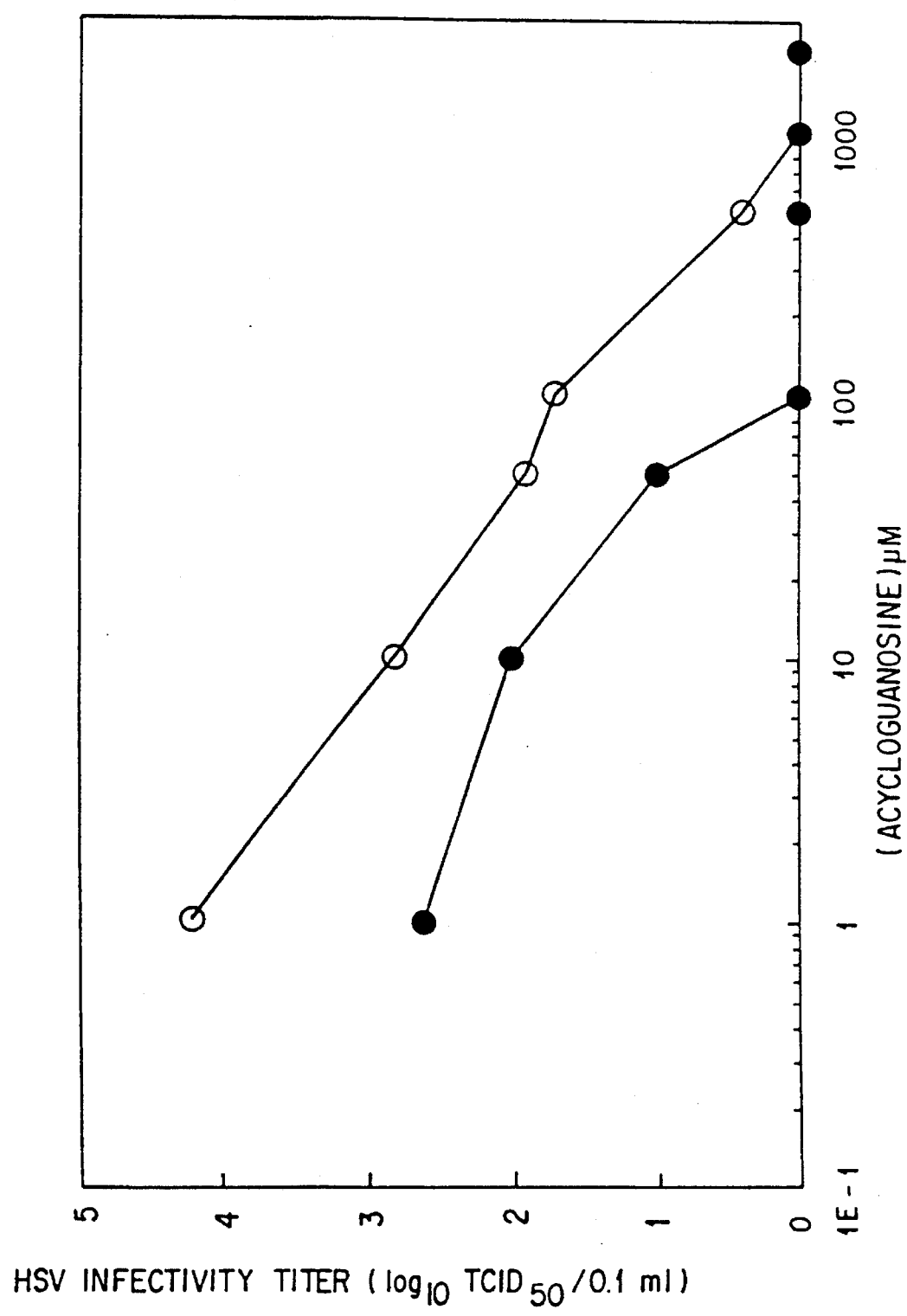
FIG. 2 Leukoregulin (LR) enhancement of ACG inhibition of infectious HSV-1 virus production by WISH cells. WISH cells were treated for 2 hours with the indicated concentrations of ACG or with ACG and 5 units leukoregulin/ml 3 hours after infection with HSV-1. The WISH cell culture medium was assayed after 24 hours for the presence of HSV-1. (o) ACG treated, (●) ACG+leukoregulin treated.

The initial study demonstrated that leukoregulin, when added simultaneously with 1 to 100 μM ACG, produces a further 1–2 log decrease in the production of infectious HSV-1 compared to the inhibition by ACG alone (FIG. 2). Pre-treatment of the HSV-1 infected WISH cells with leukoregulin 30 min. prior to ACG, a period sufficient for leukoregulin to initiate increased target cell membrane permeability (Barnett et al, Cancer Res. 1986, 46:2686–92), produces a significant but a much smaller, i.e., <1 log, decrease in HSV-1 infectious virus production compared to ACG alone and only at 100 μM ACG.

The data generated from two separate additional experiments of WISH cells treated with leukoregulin and ACG 3 hours after HSV-1 infection are summarized in FIG. 3. The presence of leukoregulin alone (upper left panel) does not significantly alter HSV-1 infectivity. Virus infectivity diminishes from $10^{3.2}$ $TCID_{50}/ml$ to $10^{2.0}$ $TCID_{50}/ml$ in the presence of 100 μM ACG ($p<0.001$). The addition of leukoregulin augments the decrease in virus infectivity to $10^{0.9}$ $TCID_{50}/ml$ ($p<0.001$). These data clearly show that leukoregulin can enhance the ability of ACG to inhibit HSV-1 virus replication. Moreover, the concentration of ACG required to decrease the production of infectious virus is greatly reduced as much as 10 fold or more when leukoregulin is present. If leukoregulin (5 u/ml) is left on the cells for 24 hours (that is, the duration of the assay), complete inhibition of viral production is observed in the absence of the anti-viral chemotherapeutic agent.

To further assess the efficacy of leukoregulin in inhibiting HSV replication, a HSV-1 plaque assay was used to determine the concentration of ACG and leukoregulin which inhibit HSV-1 plaque formation by 50%, expressed as the mean 50% inhibitory dose ($ID_{50}$). HSV-1 was inhibited by ACG alone at a $ID_{50}$ of 16 μM. The presence of 5 units of leukoregulin reduced the $ID_{50}$ greater than 20 fold to 0.7 μM.

In order to evaluate the specificity of leukoregulin enhancement of ACG anti-HSV-1 action, the effect of three additional cytokines on ACG inhibition of HSV-1 infectivity was next examined. As is shown in FIG. 3, IL-1 alpha, IFN-alpha and IFN-gamma do not significantly alter the anti-viral effects of ACG. In contrast, leukoregulin significantly enhances the anti-viral effects of ACG ($p<0.001$). When IFN is added to the cells prior to virus infection, significant inhibition of virus replication is observed.

The entire contents of all of the references cited hereinabove are hereby incorporated by reference.

One skilled in the art will appreciate from a reading of the foregoing disclosure that various changes in form and detail can be made without departing from the true scope of the invention. The artisan will also appreciate that the invention may also have application to agricultural settings.

What is claimed is:

1. A method of treating a herpes virus infection in an animal consisting essentially of administering to said animal an amount of leukoregulin sufficient to reduce viral infectivity and inhibit viral production.

2. A method of treating a herpes simplex virus infection in an animal consisting essentially of administering to said animal an amount of leukoregulin sufficient to reduce viral infectivity and inhibit viral production.

* * * * *